United States Patent [19]

Ruppen et al.

[11] Patent Number: 5,068,414

[45] Date of Patent: Nov. 26, 1991

[54] HYDROXYTEREPHTHALIC ACID

[75] Inventors: Mark E. Ruppen, Martinsville; Scott Hagedorn, West Trenton, both of N.J.

[73] Assignee: Celgene Corporation, Warren, N.J.

[21] Appl. No.: 470,685

[22] Filed: Jan. 26, 1990

[51] Int. Cl.$^5$ .............................................. C07C 62/00
[52] U.S. Cl. ............................................................ 562/508
[58] Field of Search .................................................. 562/508

[56] References Cited

U.S. PATENT DOCUMENTS

| | | | |
|---|---|---|---|
| 4,283,420 | 8/1981 | Pigerol et al. | 562/508 |
| 4,693,745 | 9/1987 | Brunner | 562/508 |
| 4,841,096 | 6/1989 | Miyashita | 562/508 |

FOREIGN PATENT DOCUMENTS

| | | |
|---|---|---|
| 717096 | 8/1965 | Canada . |
| 131738 | 8/1982 | Japan . |
| 131739 | 8/1982 | Japan . |

*Primary Examiner*—Paul J. Killos
*Attorney, Agent, or Firm*—Mathews, Woodbridge & Collins

[57] ABSTRACT

1,2-Dihydroxycyclohexa-3,5-diene-1,4-dicarboxylic acid and its salts, which are novel intermediates yielding hydroxyterephthalic acid upon dehydration, can be prepared by culturing terephthalic acid and a carbon/energy source with a microorganism capable of oxidizing terephthalic acid but incapable of degradation of 1,2-dihydroxycyclohexa-3,5-diene-1,4-dicarboxylic acid thereby formed.

2 Claims, No Drawings

HYDROXYTEREPHTHALIC ACID

The present invention pertains to the preparation of hydroxyterephthalic acid, salts thereof, and to intermediates useful therein.

Terephthalic acid is a bulk commodity used in the preparation of various polymers such as polyesters formed with glycols. Hydroxyterephthalic acid, or 2-hydroxybenzene-1,4-dicarboxylic acid is employed similarly when it is desirable to include a functional group in the final polymer. In contrast to terephthalic acid, hydroxyterephthalic acid is relatively expensive.

The present invention pertains to a process for the economical preparation of hydroxyterephthalic acid, herein referred to as 2-hydroxybenzene-1,4-dicarboxylic acid, and its salts. In broadest sense, it involves subjecting 1,2-dihydroxycyclohexa-3,5-diene-1,4-dicarboxylic acid, which can be depicted by the formula:

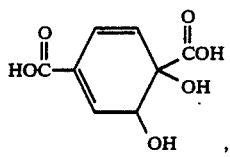

or a salt thereof to dehydration.

The dehydration can be catalyzed by either acid or base. In the first instance, 1,2-dihydroxycyclohexa-3,5-diene-1,4-dicarboxylic acid is simply treated with an acid; in the second, dihydroxycyclohexa-3,5-diene-1,4-dicarboxylic acid is dissolved in base to form a salt thereof. Either dehydration reaction can be accelerated by the application of heat, typically employing temperatures of from 60° to 90° C. Any relatively strong acid such as sulfuric acid or hydrochloric acid, or any relatively strong base such as sodium hydroxide or potassium hydroxide can be employed. The dehydration is readily followed by UV, the starting material absorbing at 270 nm (pH 7.0) whereas 2-hydroxybenzene-1,4-dicarboxylic acid exhibits peaks at 311 and 247 nm (pH 7.0).

When dehydration is performed using an acid catalyst, the product will precipitate and can be collected and readily purified, if desired, by dissolution in base and reacidification, optionally with decolorization as with activated carbon or charcoal. When dehydration is performed using a basic catalyst, the product will be formed as the salt of the base cation. The free acid can be isolated by acidification, and, if desired, purified as described above. Since some applications do not require purified material, it is possible in such cases to simply isolate the crude 2-hydroxybenzene-1,4-dicarboxylic acid or its salt formed in the dehydration step without further purification. Of the two methods, basic catalysis is somewhat preferable when highly purified material is required since acidic catalysis may produce small amounts (from 0 to 10%) of 4-hydroxybenzoic acid as a side product.

Because hydroxyterephthalic acid as the free acid is relatively insoluble in most organic solvents, the salts thereof often are more convenient to work with. Such salts include those with bases such as the alkali metals, alkaline earth metals, non-toxic metals, ammonium, and mono-, di- and trisubstituted amines, such as for example the sodium, potassium, lithium, calcium, magnesium, aluminum, zinc, ammonium, trimethylammonium, triethanolammonium, pyridinium, and substituted pyridinium salts.

1,2-Dihydroxycyclohexa-3,5-diene-1,4-dicarboxylic acid is a new compound which, in another aspect of the invention, is produced from terephthalic acid by a microbiological process. Briefly the microbiological process involves the use of bacterial mutants which oxidize terephthalic acid to a diol intermediate but which lack the ability to further metabolize the diol thus formed. Enzymes known to convert benzoate to 1,2-diols cannot utilize terephthalate as a substrate and conversely, the enzymes suitable for use in the present invention do not oxidize benzoate.

Mutant selection involves initial identification of strains which can utilize terephthalic acid as the sole carbon source. The first step of the procedure is performed by screening for growth on a minimal salt agar medium containing terephthalic acid to select wild-type strains which utilize this material as a carbon source.

Selected strains can be subjected to the action of a physical, chemical, or biological mutagenic agent such as exposure to UV radiation, to chemical agents such as N-methyl-N'-nitroso-N-nitrosoguanidine or ethyl methanesulfonate, or biologically through the use of transposons. See in general, *Manual of Methods for General Bacteriology*, P. Gerhardt, Ed., American Soc. for Microbiol, 1981, Chapter 13.

The mutagenized strains then are counterselected by culturing in minimal medium in the presence of terephthalic acid and one or more antibiotics which interfere with formation of normal cell wall structure, such as cycloserine, thienamycin, penicillin, carbenicillin, etc. to select for mutants which are deficient in their ability to use terephthalic acid as a carbon source. Following incubation, the cells are collected and resuspended in minimal medium containing 3,4-dihydroxybenzoate to permit outgrowth of the surviving organisms. These general procedures also are well known. See *Manual of Methods for General Bacteriology, supra*.

This counterselection procedure can be repeated several times, although mutants suitable for the present purpose generally can be obtained in the first cycle. The desired mutants are readily identified by culturing on solid media containing terephthalic acid and a growth-limiting concentration (0.5 mM) of succinate. Desired mutants, those which are unable to utilize terephthalate, thus present petite colonies whereas while wild-type strains utilizing terephthalic acid present large colonies because of their ability to utilize both terephthalate and succinate.

In the actual preparation of 1,2-dihydroxycyclohexa-3,5-diene-1,4-dicarboxylic acid from terephthalic acid, the selected strain is cultured in minimal medium in the presence a carbon/energy source such as glucose, succinate, acetate, gluconate, etc. or in a complex medium such as Luria broth, in either case in the presence of terephthalic acid.

Minimal salts media preferably are utilized in all culturing procedures. A typical composition contains 0.6 g/L of disodium phosphate, 0.3 g/L of monopotassium phosphate, 0.5 g/L of sodium chloride, 0.1 g/L of ammonium chloride, 0.1 mmol/L of calcium chloride, and 1 mmol/L of magnesium sulfate, in distilled water.

A culture of a suitable organism, a spontaneous mutant of Pseudomonas, has been deposited as ATCC No. 53938.

The following examples will serve to further typify the nature of this invention without being construed as a limitation on the scope thereof which is defined solely by the appended claims.

EXAMPLE 1

A bacterial strain capable of utilizing terephthalic acid as its sole carbon source was isolated from common soil (New Jersey) using traditional methods of enrichment culturing. The organism displayed the following characteristics: Gram negative rod; motile; does not hydrolyze gelatin; does not grow at 37° C.; catalase positive; oxidase positive; and produces fluorescent pigments. It was identified as a Pseudomonas as described in Bergey's Manual of Systematic Bacteriology. The particular isolate was designated CEL 2376.

CEL 2376 was grown in 50 mL of minimal medium containing 10 mM of terephthalic acid as the sole source of carbon. Thienamycin was added to the culture at mid-log phase ($\sim$0.2 $A_{660}$) to a final concentration of 10 μg/mL. After incubation for 4 hours at 30° C., the cells were collected by centrifugation, resuspended in minimal medium containing 3,4-dihydroxybenzoate, and incubated for fifteen hours.

After three counterselections as described in the foregoing paragraph, the surviving organisms were plated out on minimal medium containing 10 mM of terephthalic acid and a growth-limiting concentration (0.5 mM) of succinate. The desired mutants which are unable to utilize terephthalate can be identified as petite colonies while wild-type strains utilizing terephthalic acid form large colonies (because of their ability to utilize both terephthalate and succinate).

EXAMPLE 2

A mutant produced according to Example 1 (CEL 2800) was grown in one L of minimal medium containing 5 mM of glucose and 10 mM of terephthalic acid. After incubation for 72 hours at 30° C., the formation and accumulation of 1,2-dihydroxycyclohexa-3,5-diene-1,4dicarboxylic acid as the sodium salt was observed. $UV_{max}=270$ nm (pH 7.0), $\epsilon_{270}=4.5$ mM$^{-1}$ cm$^{-1}$.

The cells were removed by centrifugation and the diol-containing supernatant was applied to a Dowex AGl-X column (Cl$^-$) which had been equilibrated with deionized water. After being washed extensively with water, a linear gradient of 0 to 1 M aqueous potassium chloride was applied and the diol containing fractions were pooled and evaporated to yield 1,2-dihydroxycyclohexa-3,5-diene-1,4-dicarboxylic acid. $^1$NMR (D$_2$O) δ 5.0 (1H), 5.9 (1H), 6.45 (1H), and 6.55 (1H).

The foregoing diol can be dehydrated directly or stored at −20° C. in solution form.

EXAMPLE 3

A solution of 100 mg of 1,2-dihydroxycyclohexa-3,5-diene-1,4-dicarboxylic acid in 5 mL of 5% sulfuric acid is heated at 85° C. for 60 minutes. The solid which forms is collected (by filtration or centrifugation). The filtrate shows the absence of the 270 nm absorbance. The solid is dissolved in 1 N sodium hydroxide, filtered, and the filtrate acidified with acetic acid. The solid is collected and dried to yield 2-hydroxybenzene-1,4-dicarboxylic acid. m.p. >300° C. $^1$NMR (d$_6$-DMSO) δ 7.42 (1H), 7.45 (1H), 7.88 (1H). $UV_{max}=311$, 247 nm (pH 7.0), $\epsilon_{311}=4.1$ mM$^{-1}$ cm$^{-1}$.

Calc. for $C_8H_6O_5$: C, 52.7; H, 3.3; Found: C, 52.49; H, 3.25.

EXAMPLE 4

The sodium salt of 1,2-dihydroxycyclohexa-3,5-diene-1,4-dicarboxylic acid is prepared by dissolving 100 mg of the free acid in 5 mL of 1 N sodium hydroxide. This salt, without isolation from the aqueous solution, is heated at 85° C. for 20 minutes. The solution then is acidified with sulfuric acid and the solid which forms collected and dried to yield 2-hydroxybenzene-1,4-dicarboxylic acid, which is identical to the material produced in Example 3.

What is claimed is:

1. A compound selected from the group consisting of 1,2-dihydroxycyclohexa-3,5-diene-1,4-dicarboxylic acid of the formula:

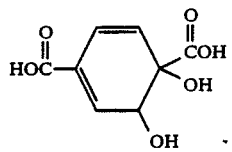

and the salts thereof with non-toxic metals, ammonium, and mono-, di- and trisubstituted amines.

2. The compound according to claim 1 which is sodium 1,2-dihydroxycyclohexa-3,5-diene-1,4-dicarboxylate.

* * * * *